United States Patent [19]
Riviere et al.

[11] Patent Number: 5,362,756
[45] Date of Patent: Nov. 8, 1994

[54] USE OF FEDOTOZINE IN THE TREATMENT OF FUNCTIONAL STATES OF INTESTINAL OBSTRUCTIONS

[76] Inventors: Pierre J. M. Riviere, 9, Rue des Arquebusiers, 75003 Paris; Xavier B. Pascaud, 41, Rue de Charenton, 75012 Paris; Francois J. Roman, 11, Allée Pierre-Fresnay, 94400 Vitry-sur-Seine; Jean-Louis Junien, 36, Avenue Eiffel, 92310 Sevres, all of France

[21] Appl. No.: 937,127

[22] Filed: Aug. 31, 1992

Related U.S. Application Data

[63] Continuation-in-part of Ser. No. 931,994, Aug. 19, 1992, Pat. No. 5,266,599, and a continuation-in-part of Ser. No. 931,957, Aug. 19, 1992, Pat. No. 5,245,080, each is a continuation-in-part of Ser. No. 367,603, Jun. 19, 1989, abandoned.

[30] Foreign Application Priority Data

Feb. 20, 1989 [FR] France ................. 89 02177

[51] Int. Cl.$^5$ ..................... A61K 31/135
[52] U.S. Cl. ........................... 514/651
[58] Field of Search ....................... 514/651

[56] References Cited

PUBLICATIONS

Reyntjens et al, "Cisapride in the treatment of chronic intestinal pseudo-obstruction", Z Gastroenterol (Suppl. 1) 1990; 28: 79–84 79.
McCallum et al, "Cisapride—A Preliminary Review of its Pharmacodynamic and Pharmacokinetic Properties, . . . " Drugs 36: 652–681 (1988), 0012-6667/88/00-12-0652.
Livingston et al, "Postoperative Ileus", Digestive Diseases and Sciences, vol. 35, No. 1 (1990), pp. 121–132.
MacColl et al, "Treatment of Acute Colonic Pseudoobstruction (Ogilvie's Syndrome) With Cisapride", Gastroenterology, vol. 98, No. 3, 1990, pp. 773–776.
Miller et al, "Accurate Measurement of Intestinal Transit in the Rat", Journal of Pharmacological Methods 6, 211–217 (1981).
Holzer et al, "Inhibition of Gastrointestinal Transit Due to Surgical Trauma or Peritoneal Irritation is Reduced in Capsaicin-Treated Rats", Gastroenterology 1986, vol. 2, 91:360–3.
Clevers et al, "Restoration of Gastrointestinal Transit and Colonic Motility after Major Abdominal Surger; Effects of Cisapride", Surg. Res. Comm, 1988, vol. 4, pp. 205–213.
Homerin et al, "Efficacy of Fedotozine in Non-ulcer Dyspepsia a Double-Blind Dose-Range Controlled Trial", Abstracts of World Congresses of Gastroenterology, 1990. p. 455.
Bost et al, "Effect of Fedotozine of Esophageal Motility in Healthy Volunteers", European Journal of Gastroenterology & Hepatology 1991, vol. 3 (Suppl. 1) S13.
Pascaud et al, "Effet De La Fedotozine Sur L'Inhibition De L'Evacuation Gastrique Et Du Transit Intestinal Dans L'Ileus Adynamique Experimental Chez Le Rat", Gastroenterol. Clin. Biol., 1992, 16.
Haas et al, "Iga Antigliadines Fecales: Un Marqueur Non Marqueur Non Invasif Du Diagnostic Et Du Suivi De La Maladie Coeliaque", Gastroenterol. Clin. Biol., 1992, 16 A 133.
Pascaud et al, "Fedotozine Restores Normal Gastric Emptying and Intestinal Transit in Experimentally Induced Ileus in Rats", Journal of Gastrointestinal Motility, vol. 3, No. 3, Sep. 1991, 194 Abstracts.
Riviere et al, "Fedotozine Restores a Normal Intestinal Motility Pattern in Experimentally Induced Ileus in Rats", Journal of Gastrointestinal Motility vol. 3, No. 3, Sep. 1991, Abstracts 197.
Pascaud et al, "Effects of Fedotozine on Gastrointestinal Motility in Dogs: Mechanism of Action and Related Pharmacokinetics", J. Pharm. Pharmacol., 1990 42:546–552.

Primary Examiner—Marianne M. Cintins
Assistant Examiner—William R. A. Jarvis

[57] ABSTRACT

A process for inhibiting functional ileus in a patient, which consists of administering a therapeutically effective dose of (+)-1-1[(3,4,5-trimethoxy)benzyloxymethyl]-1-phenyl-N,N dimethylpropylamine or the addition salt thereof with (−)-tartaric acid is disclosed.

6 Claims, No Drawings

USE OF FEDOTOZINE IN THE TREATMENT OF FUNCTIONAL STATES OF INTESTINAL OBSTRUCTIONS

CROSS REFERENCE TO RELATED APPLICATIONS

This application is a continuation-in-part of application Ser. No. 07/931,994, filed Aug. 19, 1992, now U.S. Pat. No. 5,266,599, and application Ser. No. 07/931,957, filed Aug. 19, 1992, now U.S. Pat. No. 5,245,080, each of which is a continuation in-part of application Ser. No. 07/367,603, filed Jun. 19, 1989, abandoned.

In gastroenterology it is known that functional occlusions observed at different stages of the gastrointestinal tract result in a motor paralysis of the digestive tract. These states, known as ileus, are always observed, inter alia, after certain surgical operations, especially laparotomies. They may also be encountered in localised functional occlusive disorders such as pseudo obstructions of the colon (Ogilvie syndrome), more extensive occlusions such as chronic iodapathic pseudo obstruction which corresponds to a true gastrointestinal paralysis, or in various retroperitoneal disorders such as nephritic colics, in which persistent ileus may be established, linked with peritoneal irritation.

Whatever the ethiologic circumstances, these ileus result in a build-up of gases and secretions which cause painful abdominal meteorism, nausea and vomiting in the patient. A distinction is drawn depending on the duration of these states, which is about 72 hours for "simple" or "physiologic" post-operative ileus and up to several weeks for cases of paralytic ileus where an underlying trouble, for instance a hydroelectric trouble should be investigated. The latter cases are the more serious and the patent frequently has respiratory problems linked with the meteorism and the conditions of dehydration for which the symptomatic medical treatment in a hospital environment consists of inserting a nasointestinal tube, in conjunction with rehydration of the patient by intravenous route until the ileus is resolved.

Apart from its traumatic aspect, this treatment is a hindrance to the reintroduction and/or removal of any gastric probe which may be used and also extends the time which the patient spends in bed or indeed in hospital. Edward H. Livingstone, MD and colleagues (Postoperative Ileus—Digestive Diseases and sciences, Vol. 35, No. 1 (Jan. 15, 1990) pp 121-132) report alternative treatments which have been proposed without any convincing success.

Thus, attempts to reestablish intestinal motility after postoperative ileus by electrical stimulation or the external use of magnetic energy have failed. Treatments seeking to inhibit the release of mediators of the adrenergic system which are involved in postoperative ileus have been proposed, without achieving satisfactory solutions. In fact, at the doses at which they are active, the adrenergic inhibitors cause secondary cardiovascular effects which are dangerous to patients in postoperative situations.

Similarly, in order to inhibit these adrenergic mediators, treatments have been proposed which are difficult to perform, such as the instillation of local anaesthetics during surgery or the administration of prostaglandins, the effect of which varies depending on the method of administration, the intravenous route having proved the most appropriate.

Other treatments set out to activate intestinal tone and the peristaltic action. To this end, parasympathomimetic compounds have been used or opiates capable of reestablishing the occurrence of migrating myoelectric complexes (MMC) at the duodenal level. Apart from their harmful side effects, these treatments have proved doubtful. Modifiers of the motility of the gastrointestinal tract have also been proposed, especially metoclopramide (DCI), for which contradictory results were obtained in the treatment of postoperative ileus and which is also known to have extrapyramadal side effects.

Cisapride (DCI) is cis-4-amino-5-chloro-N-[1-[3-(4-fluorophenoxy)propyl]-3-methoxy-4-piperidinyl]-2-methoxybenzamide, which is chemically related to metoclopramide. The stimulating effects on peristaltic action exerted by this product have been explored thoroughly in the gastrointestinal tract (Drugs-Cisapride: A Preliminary Review, Vol. 36, 6, 1988 pp.652–681). The use thereof by oral route is particularly indicated for cases of gastro-oesophageal reflux, oesophagitis by gastro-oesophageal reflux and for complaints linked to a delay in gastric evacuation.

In the review mentioned above, the pharmacodynamic properties presented tend to demonstrate that the product would increase gastrointestinal motility along the entire tract in general. Thus, Cisapride would increase the motility of the oesophagus and the pressure of its sphincter, would accelerate gastric draining and would thus reduce the time taken for solids to pass through patients suffering from gastroparesia of various origins; equally, the product would reduce the threshold of the volume needed to stimulate the gastric antrum, would establish interdigestive gastric motility comparable to that caused naturally by the migrating motor complex and finally it would significantly reduce the transit time in the intestine. Apparently, these properties ought to enable Cisapride to alleviate ileus, thus: M. VERLINDEN et al. (Br. J. Surg. 1987, 74, pp. 614–617), of the Company who market the product, conclude that it is useful to treat with repeated doses in order to remedy states of prolonged postoperative ileus, particularly in patients who have undergone an intervention by intraperitoneal route, but C. Von Ritter et al. (South African Journal of Surgery, Vol., 25, March 87 pp. 19–21), writing independently, conclude that Cisapride is ineffective in reducing the duration of postoperative paralytic ileus, and finally G. J. Clervers et al. (Surg. Res. Comm. 1988, Vol. 4, pp. 205-213) observe that the product is only relatively effective in restoring gastrointestinal transit and motility of the colon after major abdominal surgery. Furthermore Cisapride is available only for the oral route. This state of affairs is largely sufficient to cast doubt on the effectiveness of Cisapride in remedying states of ileus and restoring motility and gastrointestinal transit in spite of the fact that it would be active along the entire gastrointestinal tract, irrespective of its mechanism of activity.

Now, overcoming the difficulties encountered in this prior art and particularly the risks as to the ineffectiveness of Cisapride in remedying states of ileus, it has now been found that fedotozine (prop. INNM) which is (+)-1-[(3,4,5-trimethoxy)benzyloxymethyl]-1-phenyl-N,N-dimethyl-n-propylamine, in addition to its stimulating effect on gastric emptying and its spasmolytic activity which have already been described, surprisingly and unexpectedly makes it possible to reverse these cases of ileus caused by surgery or by irritational or pseudo-occlusive phenomena.

The present invention relates to a new method of treating functional ileus and their symptoms which consists of administering fedotozine or the tartrate thereof in a suitable quantity to safeguard or reestablish normal gastrointestinal transit in the patient, which represents a treatment of the accompanying symptoms. European Patent Application No. 0 384 088 certainly demonstrates that the object of the invention, which is (+)-1-[(3,4,5-trimethoxy)benzyloxymethyl]-1-phenyl-N,N-dimethyl-n-propylamine (−)-tartrate, referred to in this text as "fedotozine tartrate", having the formula

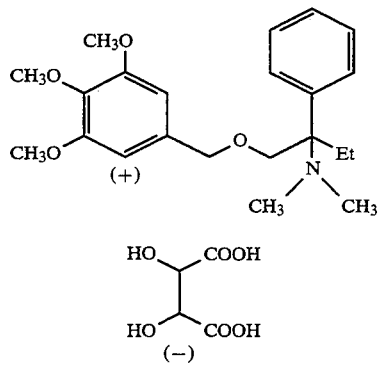

has a stimulating effect on gastric emptying combined with a spasmolytic activity which is applied to the treatment of dysfunction of the gastrointestinal tract. Complementary studies on animals have been carried out. They show that this product, by its specific affinity for the various types of opiate receptors, particularity peripheral kappa-type receptors, stimulates gastrointestinal motility, particularly in the dog, both in the gastric antrum and in the small intestines or colon (Pascaud X. et al.—J. Pharm. Pharmacol 1990, 42: 546–62). In man, these stimulant properties have been envisaged for the treatment of oesphageal reflux (Bost, R. et al. Eur. J. Gastroenterol Hepatol 1991, 3: S 13), dyspeptic conditions (Homerin, M. et al. World Cong. Gastroenterol (Aug. 26–31, Sydney) 1990, Abst PP 455). In no way did these applications give any hint of the action of fedotozine along the entire gastrointestinal tract nor, what is more, did they indicate that, unlike in the case of Cisapride, this action would make it possible to remedy ileus, whereas in spite of its alleged overall activity Cisapride does not achieve this result.

In fact, it appears that the mechanism of activity of fedotozine is connected :with a set of receptors common to every part of the tract which have the function of governing motility, whereas Cisapride, at the different levels in which its activity was observed, would have only a localised effect on a partial population of particular receptors which would be different in each section of the tract.

Now, it has been found that unexpectedly, in view of the other stimulants of peristaltic action and particularly Cisapride, fedotozine and the tartrate thereof, the preparation of which is described in European Patent Application No. 0 384 088, have the property of reestablishing tone and motility of the digestive tract in cases of functional occlusion.

The preparation of the products of this invention is described in European Patent Application No. 0 384 088 and comprises:

either of the process related to that described in U.S. Pat. No. 4,301,163, of reacting (+)-2-dimethylamino-2-phenyl-n-butanol prepared by the method described in the Japanese Patent Application published under No. 16416/1980 on May 1, 1980, with α-chloro-3,4,5-trimethoxybenzyl, or of proceeding to resolve the racemic amino ether oxide prepared as in Example 2 of U.S. Pat. No. 4,301,163 using optically active acids and notably the enantiomers of tartaric acid, which are preferred.

The studies carried out in animals which justify the use to which this invention relates are as follows:

the reversal by fedotozine and the tartrate thereof of the inhibition of gastric evacuation and gastrointestinal transit in situations of experimental ileus induced in the rat by the intraperitoneal injection of an aqueous acetic acid solution or by laparotomy and palpation of the caecum, which represent, respectively, ileus induced by, peritoneal irritation and ileus induced by surgical trauma.

The counteracting by fedotozine and the tartrate thereof of the inhibition of gastric motility induced in conscious dogs by distension produced by the insertion of a balloon into the proximal colon, this situation representing an ileus caused by pseudo-obstruction of the colon (Ogilvie syndrome).

EXPERIMENTAL SECTION

1—Reversal of Experimental Adynamic Ileus in the Rat

The studies were carried out on male Sprague-Dawley rats weighing between 180 and 250 g on which the following studies were carried out:

a) using animals equipped with electrodes placed on the small intestines, to record motility, and under the effect of the test products administered intravenously (i.v.) or subcutaneously (s.c.) the elimination of an ileus caused by laparotomy and palpation of the caecum (LPC) using the technique described by Holzer et al. (Gastroenterology 1986: 91, 360–363) or caused by the injection of a 0.6% by volume aqueous solution of acetic acid (AA), in a quantity of 10 ml/kg by intraperitoneal route using the technique described by Pairet and Ruckebusch (J. Pharm. Pharmacol. 1989: 41, 757–761).

b) on animals in which ileus had been caused by acetic acid (AA), gastric emptying (GE) and intestinal transit expressed by calculation of the geometic centre (GC) of a meal labelled with $^{51}$Cr.

In these experiments, Cisapride (DCI) and Metoclopramide (DCI) were used as comparison products.

1.a—Restoration of Intestinal Motility After Experimental Ileus

Experimental Procedure

Sprague-Dawley rats anaesthetised with sodium pentobarbital (50 mg/kg i.p.) are implanted with Ni/Cr electrodes in the muscular layer of the small intestine at 3 and 30 cm from the pylorus, the ends of the electrodes being left on the outside and secured in a protected way against the animals' skin. Three to four days after implanting, the electrodes are connected to a polygraph (DYNOGRAPH R612, Beckman) to record the electrical activity of the small intestine. The signal obtained is integrated according to a time base of 20 seconds and then retranscribed onto a potentiometric recorder (Linseis L6510) to aid visualisation and processing of the readout representing the digestive motility.

In fasting rats, the normal intestinal base profile is characterised by the regular occurrence every 12 to 15 minutes of migrating myoelectric complexes (MMC). The MMCs consist of successions of resting phases (phase I), phases of irregular activity (phase II) and phases of regular activity (phase III). These latter phases are characteristic and are the most noticeable on the trace and are therefore used as a measuring parameter which indicates the presence of MMC.

The induction of a surgical ileus (LPC) with the irritant (AA) suppresses these phases III for at least one hour. The test thus consists of observing the effect of the test products administered in solution by intravenous route (i.v.) or subcutaneous route (s.c.) on the eventual return and hourly rate of occurrence of the phase III considered to be an indicator of intestinal motor activity.

Test—Results

According to the references mentioned hereinbefore, the states of ileus are induced by laparotomy and palpation of the caecum (LPC) for 30 seconds, the animal having been anaesthetised by i.v. injection of pentobarbital, or else the irritable type ileus is caused by the intraperitoneal administration of a solution of acetic acid (AA) in an amount of 10 ml/kg for a solution containing 0.6% (p/v) of acid. Having been thus treated, the animals which have been observed to exhibit phase III at an hourly rate of about 4 then have a permanent ileus which eliminates all motility and consequently all type III activity phases for more than an hour.

In the test, 5 minutes after induction of the ileus (LPC or AA) the test products are administered in solution by i.v. or s.c. route and the phase III signs of regular activity are recorded over a period of one hour. The results of the study are shown in Table 1 which follows.

| Test conditions Products | Dosage mg/kg | Phase III/ hour | (n) |
|---|---|---|---|
| i) i.v. route | | | |
| Test animals | | 4.0 ± 0.9 | — |
| Control animals | | 0.0 ± 0.0 | — |
| LPC ileus - FZ | 3.0 | 2.9 ± 1.6 | — |
| AA ileus - FZ | 3.0 | 2.9 ± 1.3 | — |
| ii) s.c. route | | | |
| Test animals | | 3.89 ± 0.78 | (9) |
| Controls (LPC or AA ileus) | | 0.0 ± 0.0 | (9) |
| AA ileus - FZ | 10.0 | 3.33 ± 0.6 | (6) |
| AA ileus - Cisapride | 10.0 | 0.17 ± 0.18 | (6) |
| AA ileus - Metoclopramide | 10.0 | 0.20 ± 0.31 | (5) |

Notes:
Mean value of the phase III/hour for (n) tests;
FZ : fedotozine tartrate - dose expressed as base fedotozine.
Table 1 : Restoration of motility (Phase III/h) after experimental ileus (LPC or AA)

These results are evidence of the ability of fedotozine to inhibit experimental ileus caused in the rat. Thus, by intravenous route, irrespective of the type of ileus caused, fedotozine tartrate reestablishes about 75% of the intestinal motility, expressed as a mean rate of phase III/hour. By subcutaneous route, in a dose of 10.0 mg/kg, the product reestablishes about 85% of motility, whereas Cisapride and Metoclopramide administered in the same dose of 10.0 mg/kg reestablish only an insignificant level, less than 10%.

1.b—Inhibition of Experimental Ileus in an Animal Fed With a Meal Labelled With $^{51}Cr$ Experimental Procedure Gastric emptying (GE) and intestinal transit, expressed by calculating the geometric centre (GC) according to Miller M. F. et al. (J. Pharm Methods, 1981: 6, pp 211-217), of a liquid meal are determined after a state of ileus has been induced by the administration of acetic acid (AA) as described hereinbefore, the fedotozine tartrate being administered before or after the induction of the ileus. According to the procedure used, the test is carried out with Sprague-Dawley rats weighing from 160 to 180 g which have previously been deprived of food. Taking t=0 as the time at which the animals are force-fed, the test comprises:

for a preventive treatment against ileus, of administering fedotozine tartrate by oral route in aqueous solution at t=−60 minutes, then:

at t=−35 minutes, injecting an isotonic aqueous solution of acetic acid by intraperitoneal route in order to induce the ileus, for treatment to cure ileus, after the ileus has been induced at t=−35 minutes, fedotozine tartrate is injected by subcutaneous route in an isotonic aqueous solution in an amount of 2 ml/kg at t=−30 minutes, at t=0 the animals are force-fed with a meal consisting of 1.5 ml of whole milk containing $^{51}Cr$ as a tracer element, sacrificing the animals at t=+15 minutes and, after measuring the $^{51}Cr$ of the gastric contempts, determining the percentage of gastric emptying (GE) and determining the intestinal transit expressed by calculating the geometric centre (GC) from the measurement of the $^{51}Cr$ in ten equal segments sampled in the small intestine.

Results

Administration to prevent ileus

Under the test conditions, fedotozine tartrate has an $ED_{50}$ of 38.1 mg/kg which corresponds to the dose administered by oral route which will inhibit 50% of the effect of the ileus on gastric emptying and intestinal transit.

Administration subsequent to ileus

When administered 5 minutes after induction of the ileus, fedotozine tartrate given in a quantity of 3 mg/kg by intravenous route or 10 mg/kg by subcutaneous route restores normal motility. Results of the test carried out by subcutaneous route are given in the Table which follows. They show that the state of ileus caused by the acetic acid results in a significant inhibition, amounting to 57%, of gastric emptying (GE) and transit (GC). This ileus is inhibited by fedotozine tartrate as a function of the dosage given and is totally antagonised by the administration of the product in a dose of 10 mg/kg by subcutaneous route.

TABLE 2
REVERSAL OF EXPERIMENTAL ADYNAMIC ILEUS IN THE RAT USING FEDOTOZINE TARTRATE (s.c. route)

| | Control | Reference | Tests 1.0 mg/kg | 3.0 mg/kg | 10.0 mg/kg |
|---|---|---|---|---|---|
| Gastric emptying (GE %) | 54.6 ±8.8 | 23.4 (a) ±7.9 | 32.3 (a) ±13.2 | 39.9 (ab) ±3.8 | 52.1 (b) ±10.1 |
| Transit (GC) | 4.6 ±0.3 | 2.0 (a) ±0.3 | 2.8 (a) ±0.9 | 3.8 (ab) ±0.2 | 4.1 (b) ±0.6 |

(a) $p \leq 0.01$ based on the untreated control batch
(b) $p \leq 0.01$ based on the reference batch in a state of ileus By comparison, Cisapride and Metoclopramide were used in this test in an amount of 10 mg/kg by s.c. route. At this dosage, under normal conditions, their effect on gastric emptying and transit is indisputable. After ileus induced by acetic acid, unlike fedotozine tartrate, they are totally lacking in any activity on these parameters, as demonstrated by the results in Table 3.

TABLE 3
Effects of Cisapride and Metoclopramide on gastric emptying (GE) and intestinal transit under normal conditions (control) and after experimental ileus (AA) in the rat

| | DOSAGE (mg/kg) | Gastric emptying (GE %) | Transit (GC) | (n) |
|---|---|---|---|---|
| Control animals | | 52.1 ± 1.9 | 4.3 ± 0.1 | (18) |
| Control + Cisapride | 10.0 | 67.4 ± 4.6 | 4.5 ± 0.1 | (6) |
| Control + Metoclopramide | 10.0 | 79.7 ± 3.9 | 4.8 ± 0.1 | (6) |
| Reference animals ileus (AA) | | 23.9 ± 1.4 | 2.0 ± 0.1 | (34) |
| Ileus (AA) + Cisapride | 10.0 | 29.2 ± 6.5 | 1.8 ± 0.1 | (6) |
| Ileus (AA) + Metoclopramide | 10.0 | 25.8 ± 3.0 | 1.9 ± 0.2 | (10) |

(n) number of tests.

2—Restoration of Gastric Motility Inhibited by Distension of the Proximal Colon in the Conscious Dog In conscious dogs kept without food, distension of the proximal colon by means of a balloon causes selective inhibition of gastric motility characterised by the absence of migrating motor complex (MMC) at the gastric level. This experimental model can be regarded as representing the states of ileus caused by functional pseudo-obstructions such as that of the colon in Ogilvie syndrome. The test consists of experimental study of the restoration of motility of the tract by the action of fedotozine tartrate compared with that of substances which stimulate the peristaltic action, such as Cisapride and Metoclopramide.

Experimental Procedure

A preliminary surgical preparation consists of fitting beagles with strain gauges stitched to the gastric antrum, the proximal jejunum and the transverse colon. Caecostomy is also carried out, in order to insert a balloon (10 cm long) so that the proximal colon can be distended. After the surgery the animals' recuperation and the state of their gastrointestinal motility are checked daily by recording the contractile activity at the different points of implantation of the gauges. In the fasting dog, the normal motor activity of the intestine and stomach is characterised by the cyclic occurrence of MMC approximately every 2 hours.

The actual test consists of administering the test product by i.v. route 30 minutes after the appearance of a gastric MMC on the recorder, then 10 minutes after the substance has been administered the colon is distended for 90 minutes by introducing 60 ml of water into the balloon which has been inserted, causing a pressure of 33.0±5.4 mm of mercury, a degree of distention which does not cause any pain or discomfort to the animal and does not interfere with the heart rhythm.

Under these conditions in the untreated reference animals the distension of the colon suppresses the occurrence of the next gastric MMC and delays the occurrence of a new signal by 118% (i.e. about 2 hours) whilst intestinal motility is unaffected.

In the course of the test carried out on four animals, the i.v. administration of fedotozine tartrate in an amount of 0.05 mg/kg inhibits the gastric paralysis caused by distension of the colon by means of the balloon whereas at the same dose Cisapride and Metoclopramide have no effect.

| Treatment | Duration of gastric MMC cycle (t. min.) | |
|---|---|---|
| | undistended colon | distended colon |
| 0.9% NaCl solution | 111.7 ± 23.5 | 243.8 ± 26.1 |
| 0.05 mg/kg of Fz. T. solution | 115.0 ± 21.9(4) | 112.0 ± 23.6(4) |
| 0.05 mg/kg of Cisap. solution | 106.7 ± 25.7(4) | 210.3 ± 31.4(4) |
| 0.05 mg/kg of Metocl. solution | 126.8 ± 22.6(4) | 253.6 ± 48.9(4) |

These tests clearly show that fedotozine tartrate, in addition to its suitability to promoting gastric emptying as shown in European Application No. 0 384 088 has the unexpected and new property, in view of the other stimulants of gastric peristaltic effect, of alleviating states of functional ileus following surgical intervention or pseudo-obstructions of the transit.

This remarkable property is applied to the treatment of states of functional ileus of the gastrointestinal tract both post-operative, especially after abdominal surgery, and irritative or pseudo-obstructive.

Depending on the nature and gravity of the complaint being treated, the daily therapeutic dose is between 5 and 1000 mg and, preferably, between 25 and 500 mg of product expressed in terms of fedotozine tartrate, which may be taken in one or more doses and, preferably, by injection or perfusion for postoperative ileus treatment.

The product takes the form of conventional drug preparations such as tablets, gelatin capsules, suppositories, solutions for drinking or injection, the use of which will be determined depending on the patient's condition. For so-called "dry" galenic forms the quantity of active substance may be in the range from 5 to 80% by weight of the end product, with all the excipients being used in an amount of 95 to 20% of this weight. In so-called "aqueous" forms (solutions) the active principle may be present in an amount of from 0.1 to 20% by weight of the composition, water and various adjuvants constituting from 99.9 to 80% of the total weight of the finished preparation.

As an illustration, preparations of injectable solutions contain 0.1% (p/v) of fedotozine tartrate and coated tablets contain 30 mg of fedotozine per unit, i.e. 42 mg of tartrate.

Formulations

Injectable solutions containing 0.1% (p/v) Compounds for the preparation of 100 ml of solution:

(+) 1-[(3,4,5-trimethoxy)-benzyloxymethyl]-1-phenyl-N,N-dimethyl-n-propylamine-(−)-tartrate: 0.100 g medicinal sodium chloride: 0.850 g distilled water for injections q.s. ad: 100.0 ml

Preparation

The compounds are dissolved in about 95% of the quantity of distilled water provided for the preparation at a temperature of about 20° C., with stirring. The solution obtained is filtered over a membrane with a 22 micron mesh size, then the filtrate is made up to the exact volume with distilled water, which has also been filtered. The solution is packaged in amounts of 5 ml per ampoule which are then sealed and sterilised at 121° C. for 30 minutes.

Coated tablets containing 30 mg of fedotozine, i.e. 42 mg of tartrate per unit.

| Formula for one tablet: | |
|---|---|
| - (+)-1-[(3,4,5-trimethoxy)-benzyloxymethyl]-1-phenyl-N,N-dimethyl-n-propylamine-(−)-tartrate | 42.00 mg |
| - lactose | 52.20 mg |
| - polyvinylpyrrolidone 25 | 6.00 mg |
| - microcrystalline cellulose | 12.00 mg |
| - magnesium stearate | 0.60 mg |
| - silica gel | 1.20 mg |
| - hydroxypropylmethylcellulose | 7.92 mg |
| - titanium dioxide | 0.48 mg |

| Formula for one tablet: | |
|---|---|
| -continued | |
| total | 122.40 mg |

Preparation

Into a mixer/blender are placed
active principle
lactose
hydroxypropylcellulose.

A solution of polyvinylpyrrolidone 25 in purified water is added to the resulting mixture in order to moisten it. The mixture is granulated in an apparatus fitted with a grid with a mesh size of 2 mm, the granules are dried in a drying chamber at 50° C. and then graded by passing them through a grid with a mesh size of 1 mm. In a mixer, microcrystalline cellulose, magnesium stearate and silica gel are added to these granules. After mixing, the product is compressed in amounts of 120.0 mg per unit. Then the tablets obtained are coated in a turbine at 40° C. with an aqueous suspension of titanium dioxide and about 25% of the total hydroxypropylmethylcellulose which has been set aside in order to obtain finished coated tablets with a final average weight of 122.40 mg, each containing 42.0 mg of fedotozine tartrate, i.e. 30 mg of product expressed in terms of base fedotozine.

We claim:

1. Process for inhibiting functional ileus in a patient, which consists of administering a therapeutically effective dose of (+)-1-[(3,4,5-trimethoxy)benzyloxymethyl]-1-phenyl-N,N-dimethylpropylamine or the addition salt thereof with (−)-tartaric acid.

2. Process according to claim 1, in which the functional ileus is postoperative.

3. Process according to claim 1, in which the functional ileus is of pseudo-obstructive origin.

4. Process according to claim 1 which consists in administering a daily dose of 5 to 1000 mg to the patient.

5. Process according to claim 1, which consists in administering the substance by injection.

6. Process according to claim 1, which consists in administering the substance by perfusion.

* * * * *